United States Patent [19]

Knudsen et al.

[11] 4,258,221

[45] Mar. 24, 1981

[54] CLEAVAGE OF ALKYLENEBISPHENOLS

[75] Inventors: Ronald D. Knudsen; Geir Björnson, both of Bartlesville, Okla.

[73] Assignee: Phillips Petroleum Company, Bartlesville, Okla.

[21] Appl. No.: 28,943

[22] Filed: Apr. 11, 1979

[51] Int. Cl.$^3$ ............................................. C07C 37/52
[52] U.S. Cl. .................................. 568/806; 568/780; 568/799
[58] Field of Search .............. 568/799, 806, 780, 727, 568/772; 260/772

[56] References Cited

U.S. PATENT DOCUMENTS

| | | | |
|---|---|---|---|
| 1,768,257 | 5/1930 | Jordan | 568/782 |
| 1,784,599 | 12/1930 | Jordan | 568/782 |
| 1,786,922 | 12/1930 | Schoeller | 568/782 |
| 1,788,847 | 1/1931 | Schoeller et al. | 568/782 |
| 1,805,555 | 5/1931 | Schoeller et al. | 568/782 |
| 1,812,561 | 6/1931 | Schoeller et al. | 568/782 |
| 1,838,454 | 12/1931 | Schoeller et al. | 568/782 |
| 2,422,166 | 6/1947 | Dixon | 568/782 |
| 2,497,503 | 2/1950 | Jones | 568/806 |
| 2,841,622 | 7/1958 | Norton et al. | 568/806 |
| 3,006,969 | 10/1961 | Koetitz | 568/727 |
| 3,075,015 | 1/1963 | Jones | 568/782 |
| 3,466,337 | 9/1969 | Smith | 568/806 |
| 3,478,112 | 11/1969 | Adams et al. | 568/772 |

FOREIGN PATENT DOCUMENTS 880300  10/1961  United Kingdom .................... 568/782

OTHER PUBLICATIONS

Cook et al., "J. Chemical Soc." 1948 pp. 164–167.

Primary Examiner—Werren B. Lone

[57] ABSTRACT

Alkylenebisphenols are converted or cleaved to phenols and alkyl- and/or alkenyl-substituted phenols in good yields by contacting with hydrogen in the presence of a nickel oxide/manganese oxide/metal oxide supported catalyst. In a specific embodiment, bisphenol A is converted to isopropylphenol at high selectivity and high conversion by contacting with hydrogen in the presence of a nickel oxide/manganese oxide/magnesium oxide catalyst.

8 Claims, No Drawings

CLEAVAGE OF ALKYLENEBISPHENOLS

BACKGROUND OF THE INVENTION

This invention relates to the splitting of alkylenebisphenols. In another aspect, this invention relates to a catalytic process for the conversion of alkylenebisphenols to phenol and alkyl- and/or alkenyl-substituted phenols. In accordance with another aspect, alkylenebisphenols are cleaved in the presence of hydrogen and a catalyst comprising nickel oxide and manganese oxide and a metal oxide support. In accordance with another aspect, the effectiveness of the catalyst is improved with respect to conversion and selectivity by calcination under selected conditions.

The hydrogen atoms attached to the carbon atoms ortho or para to the carbon atom containing a hydroxyl group in phenol are highly reactive and can readily lead to substitution in these positions. Because of this high degree of reactivity, direct substitution generally yields a mixture of ortho- and para-substituted phenols which are often difficult to separate. An alternate method of preparing a phenol where substitution is in only one position is to decompose or degrade an alkylenebisphenol. This usually will give a phenol and an alkylphenol. Alkylenebisphenols such as 2,2-di(p-hydroxyphenyl) propane, referred herein as bisphenol A, have been reported as being cleaved with acids or bases to give phenol and p-isopropyl or p-isopropenylphenol. These methods are reported in U.S. Pat. Nos. 3,466,337; 3,075,015; and 2,497,503. All of these methods suffer from the disadvantage that added neutralization and/or separation steps are necessary to remove the active cleavage ingredient. U.S. Pat. No. 1,788,847 discloses the use of a carbonate or hydroxide of a metal which catalyses hydrogenations as a useful catalyst in the cleavage of bisphenol A. This process, however, requires the use of steam or an inert gas along with hydrogen to conduct the cleavage and the metal to be used is not specifically defined. Likewise, the art in J.C.S., 1948, 164-167 describes the catalytic cleavage of bisphenol A in the presence of hydrogen and a copper chromite catalyst. The yield of p-isopropylphenol is about 88 mole percent. The reaction is a batch reaction conducted over a 5 hour period at 180 atms. (2520 psig). Therefore, it is desirous to produce p-isopropylphenol or other mono-substituted phenols in high yields in a continuous process at modest or low temperatures and pressures.

An object of this invention is to provide an improved process for the cleavage of alkylenebisphenols.

Another object of this invention is to provide an effective catalyst for the cleavage of bisphenols.

Another object of this invention is to provide a process exhibiting increased conversion and increased selectivity to desired products in the conversion of alkylenebisphenols.

Other aspects, objects, and the several advantages of this invention will become apparent to one skilled in the art upon reading the specification and appended claims.

THE INVENTION

In accordance with the invention, a process is provided whereby alkylenebisphenols are cleaved to phenol and alkyl- and/or alkenyl-substituted phenols in the presence of hydrogen and a catalyst comprising nickel oxide, manganese oxide and a metal oxide support.

In accordance with one embodiment of the invention, bisphenol A is cleaved to phenol and isopropylphenol by contacting bisphenol A with hydrogen in the presence of a nickel oxide/manganese oxide/magnesium oxide catalyst.

In accordance with another embodiment of the invention, the effectiveness of a nickel oxide/manganese oxide/metal oxide supported catalyst is improved for the conversion of alkylenebisphenols by increasing the calcination temperature of the catalyst before usage whereby increased conversion of alkylenebisphenol and increased selectivity to desired products are realized.

ALKYLENEBISPHENOLS

The present invention is broadly applicable to the conversion of alkylenebisphenols to phenol and alkyl- and/or alkenyl-substituted phenols. Generally, alkylenebisphenols useful in this invention can be represented by the formula

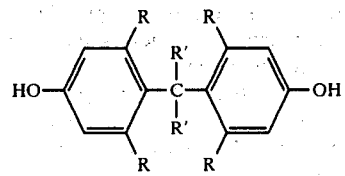

wherein R' can be a hydrogen or an alkyl, cycloalkyl, or aryl group ranging from 1 to 11 carbon atoms and R can be a hydrogen or an alkyl group ranging from 1 to 6 carbon atoms.

Typical examples of useful materials represented by the above formula are:
bis(4-hydroxy-phenyl)methane
1,1-(4,4'-dihydroxy-diphenyl)ethane
2,2-(4,4'-dihydroxy-diphenyl)propane
2,2-(4,4'-dihydroxy-diphenyl)butane
2,2-(4,4'-dihydroxy-diphenyl)pentane
2,2-(4,4'-dihydroxy-diphenyl)-4-methylpentane
3,3-(4,4'-dihydroxy-diphenyl)pentane
1,1-(4,4'-dihydroxy-diphenyl)cyclohexane
1,1-(4,4'-dihydroxy-diphenyl)-1-phenylethane
4,4'-dihydroxy-triphenyl-methane
(4,4'-dihydroxy-diphenyl)-diphenyl-methane
and the like and mixtures thereof.

CLEAVAGE CATALYSTS

The method of preparing the catalyst is not a critical feature of this invention and any known method can be used. As indicated above, it has been found that reactant conversion and product selectivity can be substantially increased by carrying out the calcination of the catalyst at an elevated temperature prior to usage. Calcination can be effected in the presence of an oxygen-containing gas or an inert gas. In a preferred embodiment, the calcined catalyst is further heated at a reduced temperature in the presence of hydrogen prior to contacting with reactant.

In one specific method of catalyst preparation, the manganese and nickel portion of the catalyst, for example, can be deposited on the metal oxide carrier through impregnation by an aqueous solution of manganese or nickel nitrate. The hydrated catalyst is then dried, preferably under vacuum, followed by calcining with air or nitrogen or mixtures thereof above 316° C. (600° F.), preferably at about 482° C. (900° F.) or higher, followed by a subsequent heating at about 350° C. or about 50° C.

above the operating temperature of the cleavage reaction for about 30 minutes in the presence of hydrogen. Hydrogen reduces the metal oxide catalyst to its lowest possible valence state while still an oxide. The initial heating or activation of these nitrate type catalysts should be done outside the reactor because of the nitrous and nitric acids formed that can be harmful to the metal reactor or metal packing.

The amount of nickel oxide (NiO) deposited on the support can be broadly about 1 to 10 wt. percent of the total catalyst system (support included) but it is preferred to be about 5 to 8 wt. percent.

The amount of manganese oxide (MnO) deposited on the support can be broadly about 10–25 wt. percent of the total catalyst system (support included) but it is preferred to be about 17–23 wt. percent.

The metal oxide support useful in this invention can be magnesium oxide, aluminum oxide, silicates or mixtures thereof. The support and/or the catalyst-support can be granular, powder, or pellet. The catalyst can be deposited on the surface of the powder, granular or pelleted support or it can be deposited on the surface of a powder or granular support followed by pelletizing. Catalyst deposited on the surface of granular or pelleted supports can be used in the current invention at about 150–300 psig below the pressure employed with powdered catalyst.

The catalyst-support can be regenerated if desired by heating in air or other oxygen-containing gas at about 482° C. (900° F.), or higher, followed by a subsequent heating at about 350°–400° C. or about 50° C. above normal operating temperatures in the presence of a slow stream of hydrogen or hydrogen-containing gas. The catalyst can be regenerated in situ.

HYDROGEN

Hydrogen gas is necessary in the catalyzed reaction described herein in order to obtain the alkyl-substituted phenols. The amount of hydrogen required is at least about 1 mole of hydrogen per 1 mole of bisphenol compound to be cleaved. Inert gases such as nitrogen can be employed along with hydrogen if desired.

SOLVENTS

The current invention can be operated with or without a solvent, but the use of a solvent is preferred because of ease of handling. Suitable solvents are primary or secondary alcohols containing 2 to 10 carbon atoms such as ethanol, n-propanol, isopropanol, butanol, pentanol, etc.; ethers such as diethyl ether and tetrahydrofuran; paraffins such as hexane, heptane; cycloparaffins such as cyclohexane, methylcyclopentane; and aromatic hydrocarbons such as toluene and xylene. It is preferred to use solvents with boiling points at least 50° C. higher or lower than the products being produced to facilitate subsequent separation by distillation. It is also preferred that tertiary alcohols not be employed as solvents since dehydration of the alcohol may occur under the conditions of the current invention. The amount of solvent employed will usually depend on the solubility of the bisphenol ingredient to be cleaved and the products obtained. Generally, saturated solvents will be used.

OPERATING CONDITIONS

The cleavage reaction for converting alkylenebisphenols is carried out under reaction conditions of temperature, pressure, and for a period of time sufficient to cause the alkylenebisphenol to be cleaved and produce phenol and alkyl- and/or alkenyl-substituted phenols. The reaction conditions and amounts of reactants can vary somewhat, but are sufficient to cause the cleavage reaction. The conditions of reactions described herein generally are as follows:

|  | Broad Range | Preferred Range |
| --- | --- | --- |
| Temperature, °F. | 482–752 | 572–707 |
| °C. | 250–400 | 300–375 |
| Pressure, psig | 100–1000 | 400–700 |
| MPa | 0.689–6.894 | 2.756–4.823 |
| Feed Rate: |  |  |
| VHSV (Vol. Hourly Space Velocity) ml feed/ml cat./hr. | 1–20 | 2–10 |
| WHSV (Wt. Hourly Space Velocity) gms. feed/gm. cat./hr. | 1–10 | 1–3 |

REACTOR

Any type of reactor, but preferably a tubular reactor of stainless steel (e.g. 316) construction, can be employed. The walls of the reactor should be free of material which will interfere with the catalyzed reaction described herein. If desired, the catalyst can be positioned in the reactor near the middle or admixed with non-catalytic material such as quartz chips in order to effect better mixing and to reduce temperature gradients therein.

REACTION MECHANISM

The exact role of the catalyst in the current invention is not known. However, it is believed that the alkylene bisphenol is first cleaved to phenol and an alkenyl-substituted phenol, the latter in the presence of hydrogen is then converted to an alkyl-substituted phenol. The following equations employing bisphenol A are used to illustrate the above-described mechanism.

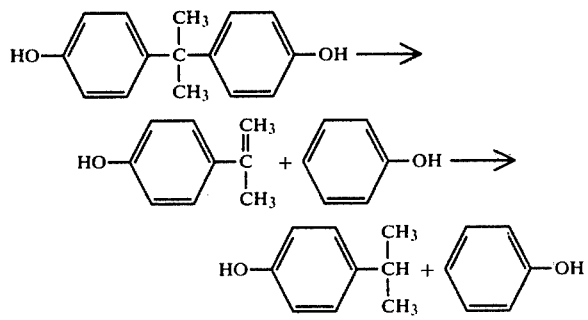

The following examples serve to illustrate the operability of the current invention.

EXAMPLE I

The following is a typical example for the preparation of the catalyst described herein. Two separate solutions were prepared, one containing 14.25 grams Ni(NO$_3$)$_2$·6-H$_2$O dissolved in 80 milliliters of water and the other containing 30 milliliters of a 50 wt. percent solution of Mn(NO$_3$)$_2$ in 30 milliliters of water. These two solutions were combined and poured slowly with stirring over 40.9 grams of MgO. The mixture was stirred for about one hour and then pressed with a spatula into a rubber motor-mount pad (6.0 inches × 6.0 inches) having approximately one-quarter inch deep grooves and allowed to dry at ambient room temperature overnight. The dried catalyst was then removed from the mold and dried at about 316° C. for 1 hour followed by heating (calcining) at 482° C. for about 2 hours during which time brown fumes were evolved. The brittle material was cooled to ambient room temperature broken into small undefined particle size and stored in a closed plastic container until ready for use. The amount of NiO present was about 7.0 wt. % and the amount of MnO present was about 20.2 wt. %.

EXAMPLE II

This example illustrates the current invention. A 316 stainless steel vertical metal tubular reactor (60.96 cm. × 1.27 cm I.D.) was filled by the following components to various heights: 1 cm. quartz glass wool on the bottom, 11 cm. copper metal pellets (0.25 cm. diameter), 6 cm. Raschig rings (0.5 cm. diameter), 1 cm. quartz glass wool, 19 cm. (about 30 milliliters) of calcined NiO/MnO/MgO catalyst described in Example I, 1 cm. quartz glass wool, 5 cm. Raschig rings, 13 cm. copper metal pellets, and 1 cm. quartz glass wool. The reactor and contents were then heated to about 50° C. above the desired operating temperature (e.g. 350° C.) while a slow stream of hydrogen was passed through the reactor at about 500 psig for 0.5–1.0 hr. to activate the catalyst. A solution of 20 grams bisphenol A dissolved in 100 milliliters of isopropyl alcohol was passed through the reactor at 350° C. and 500 psig at a rate of 160 milliliters/hr. (VHSV of about 6 milliliters feed/milliliter catalyst/hr.; WHSV 2.4 grams bisphenol A/gram catalyst/hr. along with a stream of hydrogen 8.7 liters/hr.). The effluent was then analyzed by Gas Liquid Chromatography (GLC) using a copper tube column (182 cm. × 0.476 cm.) packed with a Silicone oil (OV 210) on Chromasorb W. The column was programed by heating at 100° C. for 4 minutes and then heating to 200° C. at a rate of 30° C./min. with a 60 milliliter/min. helium flow. Table I below shows the results of this run along with other runs at lower reactor temperatures. The highest selectivity to the desired p-isopropylphenol at 100% conversion is at 350° C. The identity of p-isopropylphenol was established by comparing GLC and NMR analysis of known p-isopropylphenol samples. The para position of substitution was confirmed by treating the product along with known samples of para- and meta-isopropylphenol with Regis Regisil, bis(trimethylsilyl)trifluoroacetamide, and subjecting each to GLC analysis. The Regis Regisil derivatives of the meta- and para-isopropylphenol clearly separate as distinct peaks. The silylated product from the current invention eluted at the retention time ascribed to the para derivative with no meta derivative being present. The identity of para-isopropenylphenol was confirmed by NMR.

TABLE I

Cleavage of Bisphenol A Using a 7.0 Wt. % NiO/20 Wt. % MnO on MgO Catalyst

| Temp. °C. | % Conversion of Bisphenol A | % Selectivity by GLC[a] | |
|---|---|---|---|
| | | Isopropyl-phenol | Isopropenyl-phenol |
| 350 | 100 | 94.0 | 1.4 |
| 330 | 100 | 91.0 | 4.2 |
| 300 | 100 | 80.0 | 15.7 |
| 265 | 96.6 | 67.7 | 17.6 |
| 195 | 12.0 | 60.0 | 40.0 |

[a]GLC accuracy estimated to be ± 5%.

EXAMPLE III

This example illustrates the effects of using a similar type catalyst except less NiO is present. The procedure described in Example II was repeated but with a 4.8 wt. % NiO/21 wt. % MnO/Mgo catalyst. The catalyst was prepared in the same manner as described in Example I except 9.5 grams Ni(NO$_3$)$_2$·6 H$_2$O dissolved in 50 milliliters was employed. Nitrogen (14.2 liters/hr.) was mixed with the hydrogen (8.7 liters/hr.). Contact time was calculated to be about 11.25 mins. The results which are shown in Table II indicate a lower selectivity of isopropylphenol using the 4.8 wt. % NiO-based catalyst as compared to the 7.0 wt. % NiO-based catalyst. However, a higher selectivity to isopropenylphenol appears to occur. Phenol % conversion seems to be about the same.

TABLE II

Cleavage of Bisphenol A Using a 4.8 Wt. % NiO/21 Wt. % MnO on MgO Catalyst

| Temp. °C. | % Conversion of Bisphenol A | % Selectivity by GLC | |
|---|---|---|---|
| | | Isopropyl-phenol | Isopropenyl-phenol |
| 240 | 87.0 | 20.2 | 68.9 |
| 300 | 100 | 51.2 | 32.3 |
| 320 | 100 | 56.8 | 29.2 |
| 350 | 100 | 72.7 | 10.5 |
| 400 | 100 | 80.6 | 9.6 |

EXAMPLE IV

This example illustrates an attempt to separate the products obtained herein by distillation. The procedure described in Example III was repeated except the temperature was increased to 370° C. The total amount of feed (20 grams Bisphenol A + 100 grams isopropyl alcohol) was 582 milliliters (489 grams) pumped through the reactor in 197.59 minutes. Analysis by GLC indicated a 100% conversion with a 91% selectivity to p-isopropylphenol. The total effluent was subjected to fractional distillation at 1 mm vacuum using a short vigreaux type distillation column. Each fraction collected was analyzed by GLC and the yields of each major product calculated. Table III shows the results of this distillation.

TABLE III

Distillation and Analysis of Bisphenol Cleavage Products (1 mm Vacuum)

| Fraction | Pot Temp. °C. | Head Temp. °C. | Total Wt., gms. | Phenol | 4-Isopropyl-phenol | 4-Isopropenyl-phenol | Misc. |
|---|---|---|---|---|---|---|---|
| 1 | 80 | 45–65 | 2.72 | 2.44 | 0.07 | 0.01 | 0.20 |

Wt. of Individual Products in Each Fraction[a]

TABLE III-continued

Distillation and Analysis of Bisphenol Cleavage Products (1 mm Vacuum)

| Fraction | Pot Temp. °C. | Head Temp. °C. | Total Wt., gms. | Phenol | 4-Iso propyl- phenol | 4-Iso propenyl- phenol | Misc. |
|---|---|---|---|---|---|---|---|
| 2 | 80–100 | 70–85 | 62.07 | 37.79 | 18.40 | 1.45 | 4.43 |
| 3 | 100–105 | 85–93 | 26.31 | 0.23 | 21.88 | 0.71 | 3.49 |
| 4 | 105–155 | 93 | 1.44 | 0.01 | 0.81 | 0.24 | 0.38 |
| 5 | 155–165 | 93 | 0.29 | — | 0.11 | 0.06 | 0.12 |
| Residue | — | — | 5.88 | — | — | — | — |
| | Total weight of each product = | | | 40.47 | 41.27 | 2.47 | 8.62 |
| | | Weight % Yield = | | 98.1 | 69.2 | 4.2 | — |

Wt. of Individual Products in Each Fraction[a]

[a]Isopropyl alcohol stripped before fractionation.

EXAMPLE V

This example illustrates the amount of contact time necessary to cleave bisphenol A in 100% conversion using the catalyst described herein. The procedure described in Example III using the 4.8 wt. % NiO-based catalyst was repeated except the amount of feed was altered to provide various contact times. The amount of hydrogen passed through the reactor was proportionated. The results shown in Table IV indicate a contact time of more than 10 mins. is preferred to completely cleave the bisphenol A feed at 350° C.

TABLE IV

Effect of Contact Time on the % Conversion of Bisphenol A at 350° C. Using a 4.8 Wt. % NiO-based Catalyst

| Contact Time, Mins. | VHSV[a], ml Feed/ml Cat./hr. | WHSV[b] gms Feed/gms Cat./hr. | % Conversion of Bisphenol A | % Selectivity by GLC of p-Isopropyl- phenol |
|---|---|---|---|---|
| 4.7 | 13.3 | 5.4 | 85.0 | 67.2 |
| 6.5 | 9.6 | 3.9 | 93.0 | 74.5 |
| 10.3 | 6.0 | 2.4 | 98.7 | 78.8 |
| 26.5 | 2.3 | 1.0 | 100.0 | 79.3 |

[a]Volume Hourly Space Velocity
[b]Weight Hourly Space Velocity

EXAMPLE VI

The type of solvent employed is important in the current invention. Using a 4.8 wt. % NiO-based catalyst, the best selectivity obtained at 350° C. was when toluene was used as the solvent. However, the solubility of bisphenol A in toluene is only about 3 grams per 100 grams of solvent and, therefore, not as productive as with polar solvents such as isopropyl alcohol and acetone. Both of these polar solvents have a solubility of bisphenol A in solvent of at least 20 grams per 100 grams solvent. Bisphenol A is soluble in methyl alcohol but the cleavage reaction is not clean and as straightforward as with isopropyl alcohol. The results of the solvent study are shown in Table V listed below. Tetrahydrofuran (THF) is also a good solvent. Results using this solvent are shown in Example VII where a different catalyst form is used with a different set of reaction conditions.

TABLE V

Effects of Solvent on the Bisphenol A Cleavage Reaction Using 5. Wt. % NiO-Based Catalyst

| Solvent | Temp. °C. | Press. psig. | % Selectivity of p-Isopropylphenol |
|---|---|---|---|
| Toluene | 370 | 500 | 96.0 |
| Acetone | 360 | 500 | 73.6 |
| Isopropyl Alcohol | 350 | 500 | 72.5 |
| Methyl Alcohol | 400 | 500 | <50.0 |

EXAMPLE VII

This example illustrates the effect of using a pelletized form of catalyst rather than a powder or semi-powdered form of catalyst. MgO pellets (10–20 mesh) were treated with a $Ni(NO_3)_2 \cdot 6\ H_2O/Mn(NO_3)_2$ aqueous solution as described in Example I and the coated pellets were dried and calcined as herein described. Using the coated pellets to cleave bisphenol A dissolved in isopropyl alcohol in the manner as described in Example II, it was observed that the hydrogen pressure in the reactor has to be reduced in order to maintain a high selectivity to p-isopropylphenol. These results are listed in Table VI where it is also shown that THF is a satisfactory solvent.

TABLE VI

Effect of Pelletized NiO-Based Catalyst on Product Selectivity

| Catalyst Form | Solvent | Temp. °C. | Press., psig. | % Selectivity to p-Isopro- pylphenol |
|---|---|---|---|---|
| Semi-granular | Isopropanol | 350 | 500 | 90–94 |
| Pellet | Isopropanol | 350 | 500 | 47 |
| Pellet | Isopropanol | 350 | 300 | 67 |
| Pellet | Isopropanol | 360 | 150 | 75 |
| Pellet | THF | 360 | 500 | 79 |
| Pellet | THF | 360 | 300 | 86 |
| Pellet | THF | 360 | 150 | 75 |

EXAMPLE VIII

This example illustrates the effect of calcining the catalyst at various temperatures. A 4.8 wt. % NiO/21 wt. % MnO/MgO prepared as described in Example I was calcined at 316° C. (600° F.) and a bisphenol A/isopropanol feed passed over the catalyst in the same manner as described in Example II. The results shown in Table VII show the inventive catalyst requires calcining temperatures near 482° C. (900° F.) in order to provide higher conversions of bisphenol A and higher selectivities to p-isopropylphenol.

TABLE VII

| | Effect of Catalyst Calcining Temperature | | | |
|---|---|---|---|---|
| | Calcination at 316° C. (600° F.) | | Calcination at 482° C. (900° F.) | |
| Reaction Temp., °C. | % Conversion of Bisphenol A | % Selectivity to p-Iso-propylphenol | % Conversion of Bisphenol A | % Selectivity to p-Iso-propylphenol |
| 240 | — | — | 87.0 | 20.2 |
| 280 | 80.8 | 31.2 | — | — |
| 300 | 82.0 | 34.4 | 100 | 51.2 |
| 320 | — | — | 100 | 56.8 |
| 350 | 86.3 | 35.6 | 100 | 72.7 |
| 370 | 91.4 | 34.5 | — | — |
| 400 | — | — | 100 | 80.6 |

EXAMPLE IX

This example illustrates the current invention is operable with other type bisphenols and that the catalyst is not specific for bisphenol A. Example II was repeated except the feed contained 20 grams of 2,2-bis(4,4'-dihydroxy-diphenyl)butane dissolved in 100 milliliters of isopropyl alcohol. The cleavage reaction was conducted at 500 psig and 370° C. Analysis by GLC indicate 100% conversion of the bisphenol with selectivities of 85.3% p-sec-butylphenol and 14.7% p-sec-butenylphenol.

EXAMPLE X

This example illustrates the current invention is catalytic cleavage and not alkylation. Example II was repeated except the feed contained 20 grams of phenol dissolved in 100 milliliters of isopropyl alcohol. The reaction was carried out at 500 psig and at various temperatures. Analysis by GLC indicated very little alkylation occurs. At 220° C., 0.5% p-isopropylphenol formed; at 360° C., 2.8% p-isopropylphenol formed; at 370° C., 4.8% p-isopropylphenol formed.

EXAMPLE XI

This example illustrates that the cleavage of bisphenol A is mostly catalytic and very little thermolytic at the reaction temperatures employed in the current invention. The reaction described in Example II was repeated except the catalyst was removed and replaced with copper metal pellets (0.25 cm. diameter). At a 380° C. reaction temperature, only 14.9 wt. % of bisphenol A was cleaved (converted). At a reaction temperature of 400° C., a 19.2 wt. % conversion of bisphenol A occurred.

SUMMARY

Alkylenebisphenols can be converted or cleaved to phenols and alkyl- or alkenyl-substituted phenols in good yields by passing the alkylene-bisphenols over a NiO/MnO/MgO catalyst above 300° C. in the presence of hydrogen. For example, bisphenol A dissolved in isopropyl alcohol is converted to p-isopropylphenol in high selectivity, 94%, and high conversion, 100%, when passed at 350° C. over a catalyst based on 7.0 wt. % NiO/20 wt. % MnO/MgO support. At lower temperatures (e.g., 300° C.) the selectivity to p-isopropylphenol is 80.0% and the selectivity to p-isopropenylphenol is 15.7%.

We claim:
1. A process for splitting alkylenebisphenols which comprises contacting
   (a) at least one alkylenebisphenol represented by the formula

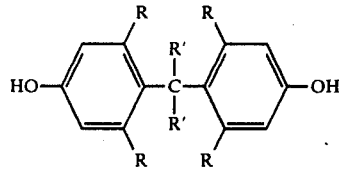

wherein R' can be hydrogen or an alkyl, cycloalkyl, or aryl group ranging from 1 to 11 carbon atoms and R can be a hydrogen or an alkyl group ranging from 1 to 6 carbon atoms with
   (b) hydrogen in the presence of
   (c) a catalytically effective amount of a catalyst consisting essentially of a mixture of nickel oxide, manganese oxide and a metal oxide support selected from the group consisting of magnesium oxide, aluminum oxide, silicates and mixtures thereof under reaction conditions of temperature, pressure and for a period of time sufficient to cause (a) to be cleaved and produce phenol and alkyl- and/or alkenyl-substituted phenols.

2. A process according to claim 1 wherein the contacting is carried out in the presence of
   (d) a solvent.

3. A process according to claim 1 wherein the amount of (b) is at least about one mole of hydrogen per one mole of alkylenebisphenol and (c) is a mixture of nickel oxide, manganese oxide and magnesium oxide.

4. A process according to claim 1 wherein (c) contains from about 1 to 10 weight percent nickel oxide, from about 10 to 25 weight percent manganese oxide and the support is magnesium oxide and is the balance of the catalyst composition.

5. A process according to claim 1 wherein (a) is bisphenol A which is cleaved to phenol and isopropylphenol and (c) is a mixture of nickel oxide, manganese oxide and magnesium oxide.

6. A process according to claim 1 wherein the temperature is in the range of about 250°-400° C., pressure is in the range of about 0.689 to 6.894 MPa and the WHSV ranges from about 1-10.

7. A process according to claim 1 for increasing reactant conversion and product selectivity which comprises calcining catalyst (c) prior to use at a temperature of at least about 900° F. in the presence of an oxygen-containing gas and then heating in the presence of a hydrogen-containing gas at a lower temperature which is about 50° F. above the subsequent operating temperature of the cleavage reaction.

8. A process according to claim 1 wherein (a) is bisphenol A, (c) is nickel oxide/manganese oxide/magnesium oxide and the contacting is carried out in the presence of a solvent of tetrahydrofuran or isopropanol and bisphenol A is converted to phenol and isopropylphenol.

* * * * *